United States Patent [19]
May

[11] Patent Number: 5,891,712
[45] Date of Patent: Apr. 6, 1999

[54] GAMETE/EMBRYO MICRO DROP CULTURE DISH

[75] Inventor: Jeffrey V. May, Wichita, Kans.

[73] Assignee: The Women's Research Institute, Wichita, Kans.

[21] Appl. No.: 976,316

[22] Filed: Nov. 21, 1997

[51] Int. Cl.⁶ .................................................. C12M 3/00
[52] U.S. Cl. .................................. 435/305.2; 435/305.3; 435/305.4; 435/288.4
[58] Field of Search ............................ 435/288.3, 288.4, 435/305.1, 305.2, 305.3, 305.4

[56] References Cited

U.S. PATENT DOCUMENTS

| | | | |
|---|---|---|---|
| 3,791,930 | 2/1974 | Saxholm | 435/288.3 |
| 4,012,288 | 3/1977 | Lyman et al. | 435/305.3 |
| 4,657,867 | 4/1987 | Guhl et al. | 435/305.3 |
| 5,700,655 | 12/1997 | Crteau et al. | 435/30 |

FOREIGN PATENT DOCUMENTS

| | | | |
|---|---|---|---|
| 357079880 A | 5/1992 | Japan | 435/288.4 |
| 404152885 | 5/1992 | Japan | 435/305.2 |

Primary Examiner—David A. Redding
Attorney, Agent, or Firm—Arent Fox Kintner Plotkin & Kahn, PLLC

[57] ABSTRACT

The present invention relates to an improved micro drop culture dish which is comprised of a substantially flat bottom surface portion and a wall portion integrally secured thereto. The bottom surface portion and wall portion are constructed of a rigid, transparent material. A plurality of circular wells having open upper surfaces are embedded into the substantially flat bottom surface portion as integral, concave indentations. These wells may also be cylindrical in shape with one end integrally attached in a perpendicular manner to the bottom surface portion. The wells may be concentrically arranged in a six-around-one manner, or in a variety of other useful patterns. The bottom surface portion may have numerical or alphabetical markings which identify individual wells for tracking purposes. This micro drop culture dish may be fitted with a detachable cover which is about 8 mm deep and of a size and shape which would allow it to cooperatively and circumferentially attach to the wall portion of the dish. The cover may have a plurality of protrusions which allow for slow gas exchange.

7 Claims, 3 Drawing Sheets

GAMETE/EMBRYO MICRO DROP CULTURE DISH

BACKGROUND OF THE INVENTION

The present invention pertains to a new device for in vitro gamete and embryo culture. The present invention is an improvement of existing gamete/embryo micro drop culture dishes, which finds particular utility by providing an innovative, cost-effective, customized means for accomplishing human assisted reproductive technology procedures, i.e., in vitro oocyte insemination and in vitro oocyte and embryo culture. This device may also be suitable for use in a variety of human and non-human embryo-related work, or in any situation that requires small volumes of medium for cell or tissue culture. In the field of culture dishes and appliances, existing devices are not specifically designed for these intended uses. There is therefore a need for a culture dish or appliance which provides small concentrically spaced wells within the confines of a larger vessel (or dish) which function to hold or maintain the integrity of small drops of fluid medium, while allowing maximal exposure to the surface area for the medium.

In a typical laboratory setting, conventional dishes used for micro drop embryo culture are planar or "flat bottomed," and of a standard 60 mm diameter. When used for gamete/embryo culture application, an aqueous medium is usually placed on the bottom of this standard dish in a series of drops, to which mineral oil or other non-aqueous fluid is added until it covers or overlays the drops. When these samples are equilibrated in an incubator, the non-aqueous overlay fluid protects the aqueous medium from potentially marked changes in pH level and temperature, but still allows for slow gas exchange, which is crucial to this process. The drops of sample material usually remain attached to the standard culture dish via surface tension. However, the drops may easily be dislodged during handling of the conventional dishes. As time passes, the drops may become increasingly easy to dislodge. Care must therefore be taken in order to prevent this dislodgement from occurring. Once dislodged, the drops may reattach, but may also move to and combine with existing drops. This corrupts the samples by changing the volume of the remaining drops, and hence the conditions that were originally established. Such an eventuality introduces variability into a procedure which demands predictability and consistency.

Other conventional culture dishes which are used in other applications utilize different methods for segregating a sample from a surrounding medium. For instance, the device disclosed in U.S. Pat. No. 3,791,930 issued to Saxholm utilizes cylindrical or rectangular supporting elements which constitute self-contained units that are separate from the culture dish. These supporting elements are inserted into an aqueous or gel-like medium so that they rest flush with the bottom of the dish, while their open upper ends extend beyond the surface of the medium. These supporting elements can be selectively inserted, removed or arranged in order to accomplish a desired application. However, the supporting elements suffer from an instability problem due to their unitary structure, which is solved by the Saxholm dish through the use of magnetic metal plates which are mounted to the underside of the supporting elements, and to the base of the dish itself, the mating of which causes the supporting elements to become attached to the dish itself.

SUMMARY OF THE INVENTION

It is therefore an object of the present invention to provide an inexpensive, easily manufactured, one-piece culture dish which, along with a cooperative one-piece cover, provides a stable, protective environment for the development of gametes/embryos during human assisted reproductive procedures.

It is a further object of the invention to provide a stable environment for a variety of embryo-related procedures or for any experiment or procedure which requires small volumes of medium for cell or tissue culture.

It is still a further object of the present invention to provide a culture dish in which the wells are arranged and marked in such a way as to provide clear identification and tracking of the samples contained therein.

It is a further object of the invention to provide a culture dish which has a one-piece lid that includes protrusions to allow gas exchange into and out of the dish.

It is yet another object of the invention to provide a culture dish which enables a shorter incubation time for the procedures.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purposes of the invention, as embodied and broadly described herein, the present invention is directed to a micro drop culture dish comprising a substantially flat interior bottom surface portion constructed of a rigid, transparent material. A wall portion is integrally secured to the substantially flat bottom surface portion and is also constructed of a rigid, transparent material.

A plurality of circular wells are embedded into the substantially flat bottom surface portion in such a manner as to constitute concave indentations in the substantially flat bottom surface. The wells may also be cylindrically-shaped, with each such well having one end integrally attached in a perpendicular manner to the bottom surface portion. The circular and cylindrically-shaped wells each have an open upper surface and a measurable depth. The wells may be arranged in a variety of ways. For instance, a well may be placed at the center of the bottom surface portion, while the remainder of the plurality of wells are equally spaced in concentric fashion around the centralized well. Each surrounding, equally spaced well may be placed 60 degrees from the center of another of the plurality of wells. The plurality of wells may also be arranged in a rectangular pattern, which is comprised of two parallel rows of three of said wells.

The bottom surface portion may contain identifying markings adjacent to each of the plurality of individual wells. A detachable cover may also be used, which is approximately 8 mm deep and of a size and shape which would allow it to cooperatively and circumferentially attach to the wall portion of the dish. The detachable cover may include a plurality of protrusions allowing the slow exchange of gas into and out of the interior of the micro drop culture dish.

The accompanying drawings, which are incorporated in and constitute a part of this specification, illustrate the embodiments of the invention and, together with the description, serve to explain the principles of the invention.

DETAILED DESCRIPTION OF THE INVENTION

Figure 1:
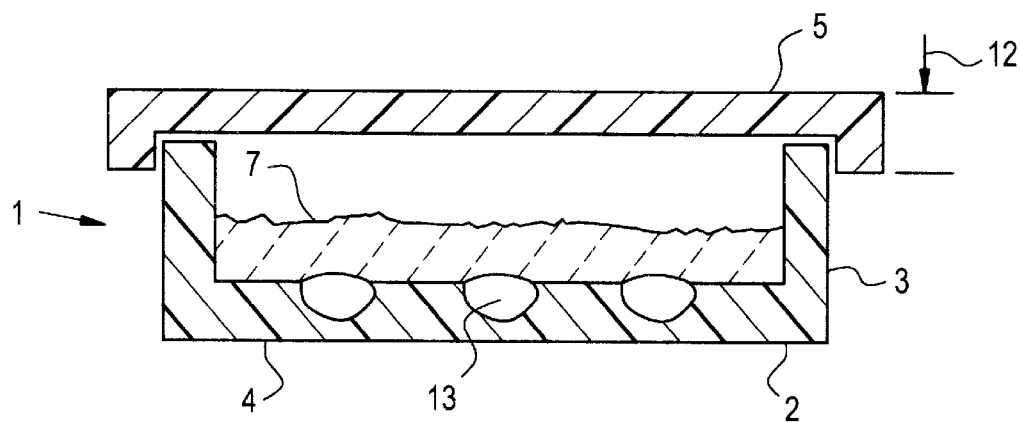
FIG. 1 illustrates a side elevational, cross-sectional view of the micro drop culture dish of the present invention and the cover.

Reference will now be made in detail to the present preferred embodiments of the invention, examples of which are illustrated in the accompanying drawings in which like reference characters, refer to corresponding elements.

Figure 2:
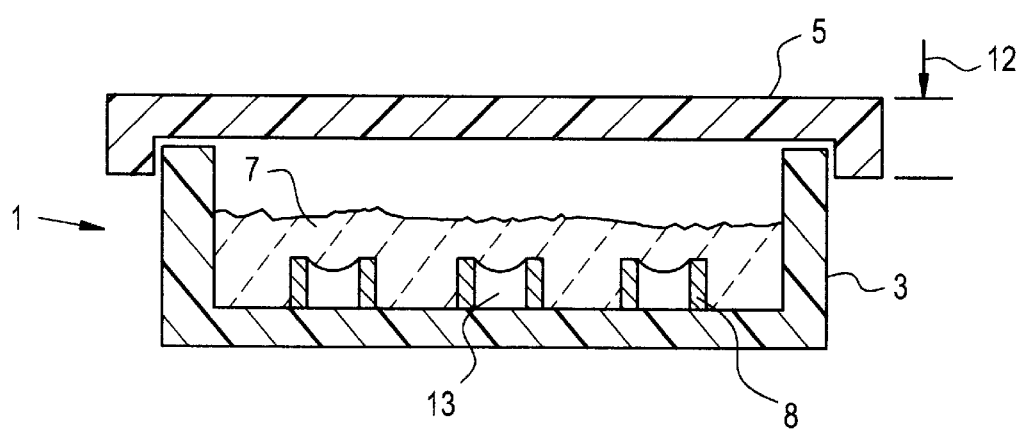
FIG. 2 illustrates a side elevational, cross-sectional view of the micro drop culture dish, the cylindrical wells and the cover.

The present invention is directed to a micro drop culture dish, which is shown generally as 1 in FIGS. 1 and 2. The micro drop culture dish 1 has an interior comprising a substantially flat bottom surface portion 2, which is constructed of a rigid, transparent material. In the preferred embodiment of the present invention, the bottom surface portion 2 is between 45 mm and 55 mm in circumference. This circumferential dimension is generally believed to be optimal for accomplishing the gamete/embryo applications intended for this invention, since it allows for the accommodation of a plurality of equally spaced wells, 4 and 8, which hold microdrops of aqueous medium 13, as well as the retention of a non-aqueous fluid media 7, which is required for the intended procedures.

A wall portion 3 is integrally secured to the substantially flat bottom surface portion 2. The wall portion 3 is also constructed of a rigid, transparent material. In the preferred embodiment, the wall portion 3 is between about 100 mm and about 12 mm in height. This height is believed to be optimal, as a result of the fact that the micro drop culture dish must have the ability to contain a non-aqueous fluid media 7, which is required to accomplish the gamete/embryo applications intended for this invention.

In the embodiment of the micro drop culture dish shown in FIG. 1, a plurality of circular wells 4 are embedded into the substantially flat bottom surface portion 2 in such a manner so as to constitute concave indentations in the substantially flat bottom surface 2. The embedded circular wells 4 allow for the retention of fluid media 13 which is crucial for the intended use of this device.

Figure 4:
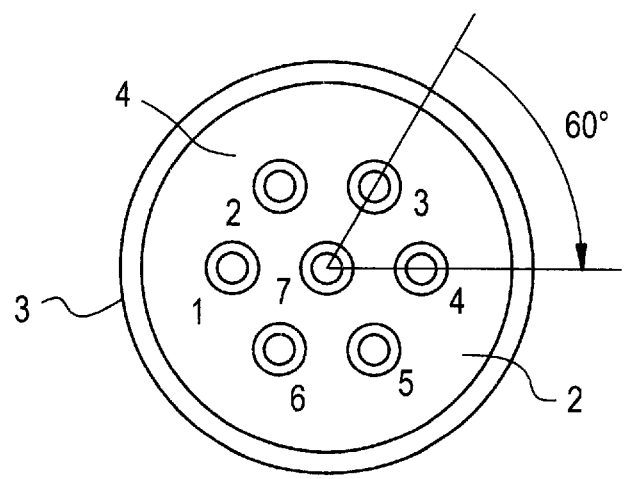
FIG. 4 illustrates a plan view of the micro drop culture dish with the wells arranged concentrically.

The plurality of circular wells 4 each have an open upper surface to allow for the efficient exchange of gases with the non-aqueous fluid media 13. The plurality of wells 4 may be arranged in a variety of manners. As shown in FIG. 4, one of the plurality of wells 4 may be placed at the center of the bottom surface portion 2, and a remainder of the plurality of wells 4 are equally spaced in concentric fashion around the centrally-located well, for example, with each of the plurality of wells 4 being 60 degrees from the center of another of the plurality of wells 4.

Figure 5:
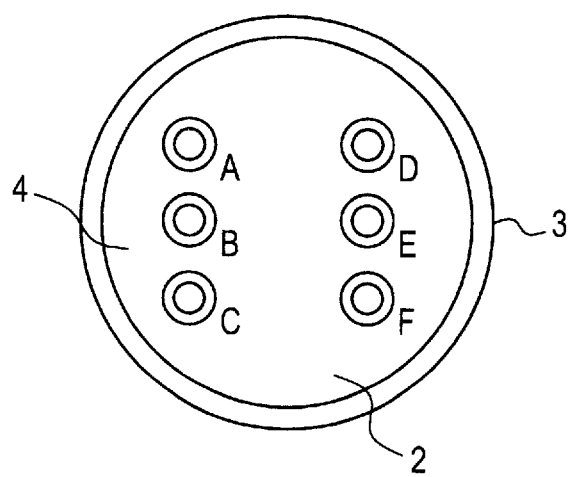
FIG. 5 illustrates a plan view of the micro drop culture dish with the wells arranged in two parallel rows.

Referring now to FIG. 5, the plurality of wells 4 may also be arranged in a rectangular pattern, which includes two parallel rows of three wells each. In addition, as shown in FIGS. 4 and 5, the bottom surface portion 2 of the micro drop culture dish 1 may contain alphabetical or numerical identifying markings adjacent to each of the plurality of wells 4, in order to facilitate tracking of the sample media.

Figure 3:
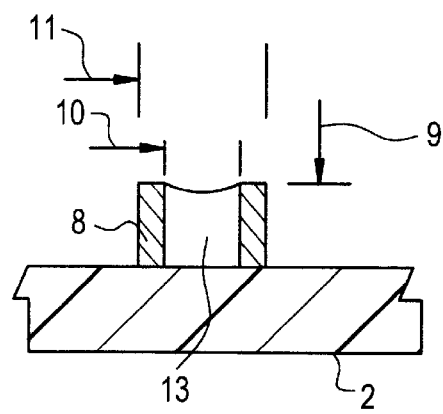
FIG. 3 illustrates a side elevational, truncated cross-sectional view of the bottom portion of the micro drop culture dish and a cylindrical well.

In another embodiment of the present invention shown in FIG. 2, the micro drop culture dish 1 may be comprised of a plurality of cylindrically-shaped wells 8. As shown in FIG. 3, each of the plurality of cylindrically-shaped wells 8 has one end integrally attached in a perpendicular manner to the bottom surface portion 2. In addition, each of the plurality of cyndrically-shaped wells 8 has an open upper surface and a depth 9. The depth 9 of each of the plurality of cylindrical wells 8 is about 1–2 mm. This depth 9 is seen as optimal, relative to the height of the wall portion 3, since in order to accomplish the intended gamete/embryo applications, a non-aqueous fluid media 7 must overlay the sample media 13 that is retained by the plurality of cylindrically-shaped wells 8. The inner diameter 10 of each of the plurality of cylindrically-shaped wells 8 is about 5 mm and the outer diameter 11 of each of the plurality of cylindrically-shaped wells 8 is about 7 mm. The inner diameter 10 and outer diameter 11 are believed to be optimal for the intended gamete/embryo applications, since they allow for a maximal surface area of the sample medium 13 to be exposed to the non-aqueous fluid medium 7 for purposes of gas exchange.

Figure 6:
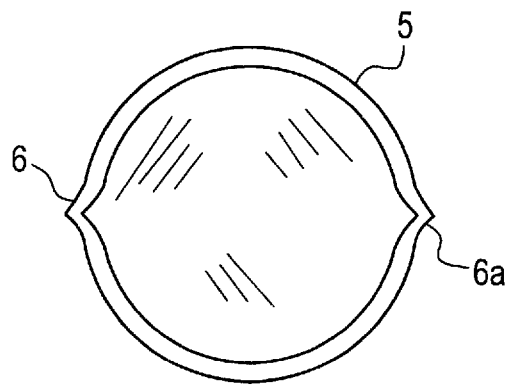
FIG. 6 illustrates a plan view of the cover for the micro drop culture dish which has protrusions which facilitate gas exchange.
Figure 7A:
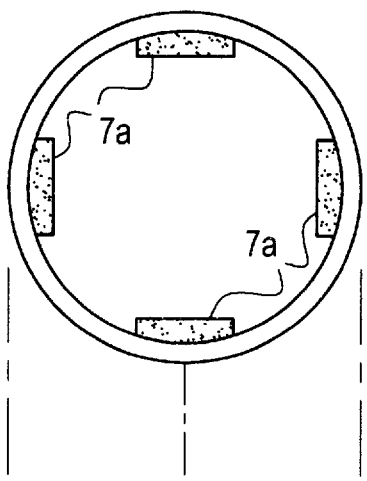
FIG. 7A illustrates another plan view of the cover for the micro drop culture dish which has protrusions to facilitate gas exchange.
Figure 7B:
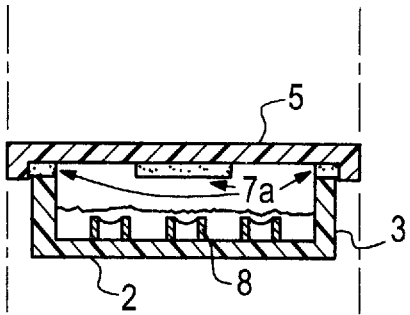
FIG. 7B illustrates a side elevational, truncated cross-sectional view of FIG. 7A.

Referring now to FIGS. 1 and 2, the micro drop culture dish may also include a detachable cover 5 which, in the preferred embodiment, has a depth 12 that is approximately 8 mm. The cover 5 is also of a size and shape which would allow it to cooperatively and circumferentially attach to wall portion 4. With reference to FIGS. 6 and 7, the detachable cover 5 may also include a plurality of protrusions 6, 6a and 7a, which block the lid from forming a tight seal thus allowing for the slow exchange of gas into and out of the interior of said micro drop culture dish 1.

As set forth above, the present invention solves many of the disadvantages found in prior culture dishes by including the small wells integrally molded into the structure of the dish itself. Aqueous media 13 can then be placed in these wells, which provide a base for a sample drop. The sample drop is effectively immobilized in such a way as to provide greater drop stability and protection for the gamete/embryo. Such stability also contributes to the maintenance of the control environment in which the sample drop is held, in terms of factors such as temperature and pH levels.

As disclosed above, the wells of the present invention are of a sufficiently small size to allow a relatively large portion of the surface area of the sample drop to maintain a significant direct contact with the non-aqueous overlay fluid for gas exchange, which is crucial to the assisted reproductive procedure. Gas exchange is further facilitated by the use of a one-piece lid which includes protrusions that allow gases to flow into and out of the dish. In addition, through the use of the wells, the process requires a smaller amount of the non-aqueous fluid overlay. The culture dish provides a more stable control environment and no time is lost for re-establishing drops which shift during transport or jarring that can occur with conventional culture dishes. The culture dish of the present invention also enables a shorter period of time for incubation of embryos.

It will be apparent to those skilled in the art that various modifications and variations can be made in the apparatus of the present invention without departing from the scope or spirit of the invention. Thus, it is intended that the present invention cover the modifications and variations provided they come within the scope of the appended claims and their equivalents.

What I claim is:

1. A micro drop culture dish having an interior comprising:
    a substantially flat bottom surface portion of said interior comprised of a rigid, transparent material;
    a plurality of circular wells, embedded into said substantially flat bottom surface portion in a manner so as to constitute concave indentations in said substantially flat bottom surface portion, said plurality of circular wells each being open on an upper surface, wherein one of said plurality of wells is placed at the center of said bottom surface portion, and a remainder of said plurality of wells are equally spaced in concentric fashion around said one of said wells;
    a wall portion comprised of a rigid, transparent material, integrally secured to said substantially flat bottom surface portion and extending above said bottom surface portion to form the dish interior; and
    a detachable cover constructed in a size and shape to allow cooperative and circumferential attachment to said wall portion and having a plurality of protrusions allowing exchange of gas into and out of said micro drop culture dish.

2. The micro drop culture dish as claimed in claim 1 wherein each of said plurality of wells are 60 degrees from the center of another of said plurality of wells.

3. The micro drop culture dish as claimed in claim 1 wherein said detachable cover is approximately 8 mm deep.

4. The micro drop culture dish as claimed in claim 3 wherein said detachable cover includes a plurality of protrusions allowing exchange of gas into and out of the interior of said micro drop culture dish.

5. A micro drop culture dish having an interior comprising:
    a substantially flat bottom surface portion of said interior comprised of a rigid, transparent material;
    a plurality of circular wells, embedded into said substantially flat bottom surface portion in a manner so as to constitute concave indentations in said substantially flat bottom surface portion, said plurality of circular wells each being open on an upper surface, wherein said plurality of wells are arranged in a rectangular pattern including two parallel rows of three of said wells;
    a wall portion comprised of a rigid, transparent material, integrally secured to said substantially flat bottom surface portion and extending above said bottom surface portion to form the dish interior, and
    a detachable cover constructed in a size and shape to allow cooperative and circumferential attachment to said wall portion and having a plurality of protrusions allowing exchange of gas into and out of said micro drop culture dish.

6. The micro drop culture dish as claimed in claim 1 wherein said bottom surface portion contains identifying markings adjacent to each of said plurality of circular wells.

7. The micro drop culture dish as claimed in claim 6 wherein said bottom surface portion is between 45 mm and 55 mm in circumference.

* * * * *